United States Patent
Suzuki et al.

(10) Patent No.: US 10,653,492 B2
(45) Date of Patent: May 19, 2020

(54) MEDICAL INSTRUMENT AND SURGICAL SYSTEM

(71) Applicant: SONY CORPORATION, Tokyo (JP)

(72) Inventors: Hiroyuki Suzuki, Tokyo (JP); Kenichiro Nagasaka, Tokyo (JP); Kazuo Hongo, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 128 days.

(21) Appl. No.: 15/746,994

(22) PCT Filed: Jun. 6, 2016

(86) PCT No.: PCT/JP2016/066746
§ 371 (c)(1),
(2) Date: Jan. 23, 2018

(87) PCT Pub. No.: WO2017/026167
PCT Pub. Date: Feb. 16, 2017

(65) Prior Publication Data
US 2018/0206930 A1  Jul. 26, 2018

(30) Foreign Application Priority Data
Aug. 10, 2015 (JP) .................. 2015-158040

(51) Int. Cl.
*A61B 34/00* (2016.01)
*A61B 90/00* (2016.01)
(Continued)

(52) U.S. Cl.
CPC .......... *A61B 34/77* (2016.02); *A61B 17/2909* (2013.01); *A61B 34/76* (2016.02);
(Continued)

(58) Field of Classification Search
CPC ......... A61B 34/71; A61B 34/76; A61B 34/77; A61B 17/29; A61B 2017/0046;
(Continued)

(56) References Cited

U.S. PATENT DOCUMENTS 7,014,642 B1 * 3/2006 Perone ............... A61B 17/44
606/122
2008/0083813 A1 * 4/2008 Zemlok .............. A61B 17/2909
227/181.1
(Continued)

FOREIGN PATENT DOCUMENTS

JP  63-147449 A   6/1988
JP  8-117228       5/1996
(Continued)

OTHER PUBLICATIONS

International Search Report dated Jul. 12, 2016 in PCT/JP2016/066746 filed Jun. 6, 2016.

*Primary Examiner* — Robert A Lynch
(74) *Attorney, Agent, or Firm* — Xsensus LLP

(57) ABSTRACT

A medical instrument according to the present disclosure includes: a contact portion configured to contact body tissue; a drive unit configured to generate drive force for causing the contact portion to contact the body tissue; and a limiter mechanism configured to impose restriction on transmission of the drive force to the contact portion, in accordance with contact force of the contact portion with respect to the body tissue. This configuration makes it possible to restrict force applied to body tissue during surgery, and to reduce failure risk, with a simple configuration.

8 Claims, 7 Drawing Sheets

(51) Int. Cl.
*A61B 17/29* (2006.01)
*A61B 17/00* (2006.01)
*A61B 34/30* (2016.01)

(52) U.S. Cl.
CPC .............. *A61B 90/03* (2016.02); *A61B 17/29* (2013.01); *A61B 34/30* (2016.02); *A61B 34/71* (2016.02); *A61B 2017/0046* (2013.01); *A61B 2017/00477* (2013.01); *A61B 2090/031* (2016.02); *A61B 2090/0812* (2016.02)

(58) Field of Classification Search
CPC ...... A61B 2017/2932; A61B 2017/294; A61B 90/03; A61B 2090/031; A61B 2090/032; A61B 2090/037
See application file for complete search history.

(56) References Cited

U.S. PATENT DOCUMENTS

2009/0209990 A1\* 8/2009 Yates ............... A61B 17/07207
606/169
2013/0304117 A1\* 11/2013 Sugiyama .......... A61B 17/0057
606/207

FOREIGN PATENT DOCUMENTS

| JP | 2003-93403 A | 4/2003 |
| JP | 2008-93437 A | 4/2008 |
| JP | 2009-500147 A | 1/2009 |
| JP | 2009-189835 A | 8/2009 |
| JP | 2014-108344 A | 6/2014 |
| WO | WO 2012/043066 A1 | 4/2012 |

\* cited by examiner

MEDICAL INSTRUMENT AND SURGICAL SYSTEM

TECHNICAL FIELD

The present disclosure relates to a medical instrument and a surgical system.

BACKGROUND ART

While a medical robotics system has advantages of improving degrees of freedom and a range of motion of a forceps in an abdominal cavity in endoscopic surgery, the medical robotics system has such a disadvantage that force sense is not fed back to an operator.

Thus, for example, the following Patent Literature 1 describes a technology of sensing force sense of a forceps end gripper, and presenting the sensed force sense to an operator. According to this technology, functional safety can be achieved by measuring grip force that is applied to body tissue by the gripper during surgery.

CITATION LIST

Patent Literature

Patent Literature 1: JP H8-117228A

DISCLOSURE OF INVENTION

Technical Problem

Nevertheless, in the technology described in the above-described Patent Literature 1, an operator needs to know in advance approximate maximum grip force to be allowed during surgery. In addition, there is such a problem that accurate grip force is not presented when a sensor is out of order. Furthermore, because a force sensor generally does not have heat resistance, pressure resistance, and humidity resistance to such a degree that cleansing and sterilization can be performed, there is such a problem that making the force sensor disposal drastically increases the cost.

For these reasons, it has been demanded to restrict force applied to body tissue during surgery, and to reduce failure risk, with a simple configuration.

Solution to Problem

According to the present disclosure, there is provided a medical instrument including: a contact portion configured to contact body tissue; a drive unit configured to generate drive force for causing the contact portion to contact the body tissue; and a limiter mechanism configured to impose restriction on transmission of the drive force to the contact portion, in accordance with contact force of the contact portion with respect to the body tissue.

A transmission unit configured to transmit the drive force generated by the drive unit, to the contact portion; a protruding portion provided on one of the transmission unit and the drive unit; and an insertion hole provided in another one of the transmission unit and the drive unit, and into which the protruding portion is to be inserted may be included. The drive force may be transmitted to the contact portion by the drive unit pulling the transmission unit, and the limiter mechanism may be formed by the protruding portion being detached from the insertion hole if contact force of the contact portion with respect to the body tissue becomes larger than a predetermined threshold.

In addition, a transmission unit configured to transmit the drive force generated by the drive unit, to the contact portion may be included. The drive unit may include a motor, and a rotation member configured to be driven by the motor to drive the transmission unit, and the limiter mechanism may be formed by the rotation member slipping with respect to rotation of the motor if contact force of the contact portion with respect to the body tissue becomes larger than a predetermined threshold.

In addition, the contact portion may include an end effector configured to grip the body tissue.

In addition, the threshold may be set in accordance with a grip target of the end effector.

In addition, the contact portion may include a pressing member configured to press the body tissue.

In addition, if the protruding portion is detached from the insertion hole, a cleansable clean region at least including the contact portion and the transmission unit may be separated.

In addition, an alarm unit configured to issue an alarm if the limiter mechanism operates may be included.

In addition, according to the present disclosure, there is provided a surgical system including: a medical instrument used for a patient; and a support arm device configured to support the medical instrument. The medical instrument includes a contact portion configured to contact body tissue, a drive unit configured to generate drive force for causing the contact portion to contact the body tissue, and a limiter mechanism configured to impose restriction on transmission of the drive force to the contact portion, in accordance with contact force of the contact portion with respect to the body tissue.

Advantageous Effects of Invention

According to the present disclosure, with a simple configuration, force applied to body tissue during surgery can be restricted, and failure risk can be reduced.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
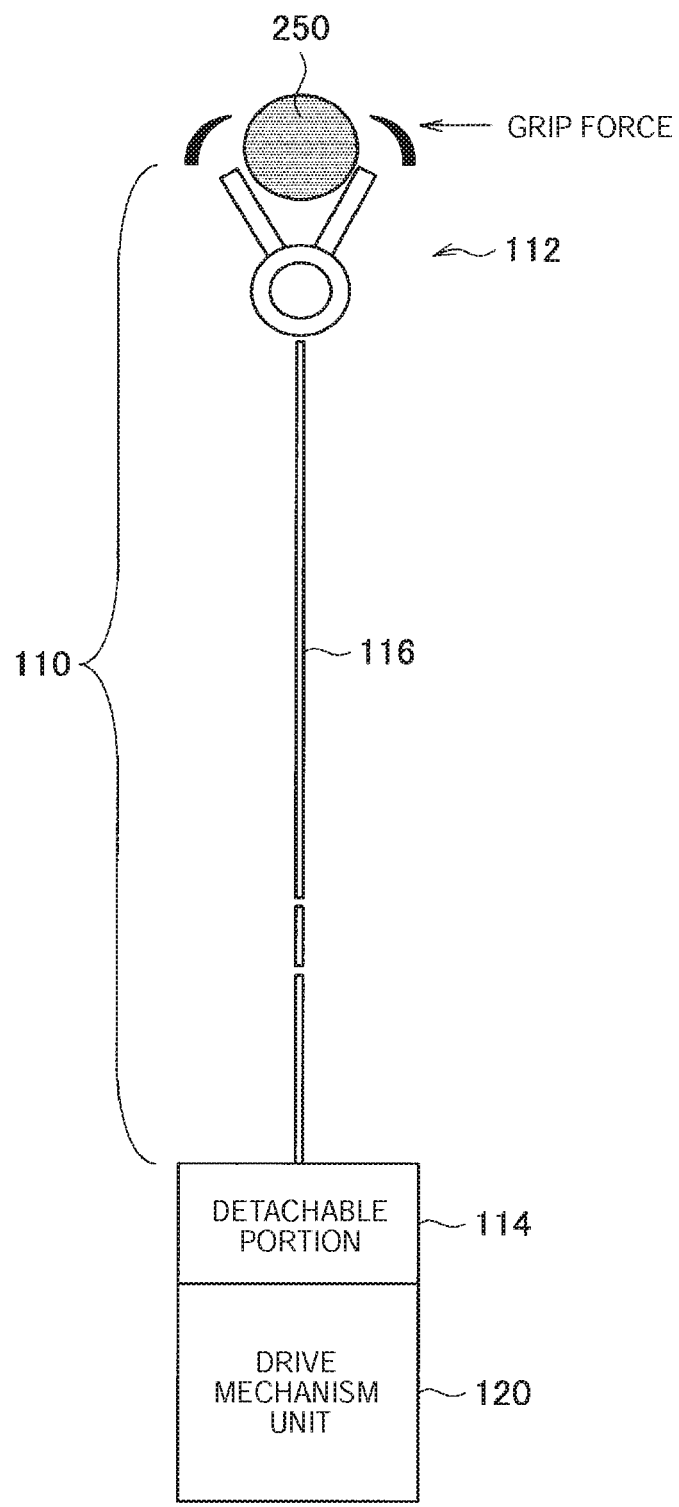
FIG. 1 is a schematic diagram illustrating a schematic configuration of a medical instrument according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

In addition, the description will be given in the following order.

1. Configuration of Medical Instrument
2. Configuration of Coupling Unit
3. Configuration of Drive Mechanism Unit
4. Example of Application to Mechanism of Driving Link Structure Using Cable
5. Configuration Example of Surgical System 1. Configuration of Medical Instrument 100

First of all, a schematic configuration of a medical instrument 100 according to an embodiment of the present disclosure will be described with reference to FIG. 1. In the present embodiment, in a clean region in which surgery is performed, a medical robotics system safely performs surgery without damaging body tissue 250, by mechanistically imposing restriction on grip force generated by a gripper.

FIG. 1 is a schematic diagram illustrating a configuration of the medical instrument 100. As illustrated in FIG. 1, the medical instrument 100 of the present embodiment includes a surgical tool unit 110 that performs surgery, and a drive mechanism unit (drive unit) 120 for driving a surgical tool. The surgical tool unit 110 has an elongated tubular shape having an end effector (a grip mechanism) 112 at a distal end, and a proximal end has a detachable portion 114 that can be separated from the drive mechanism unit 120.

Figure 2:
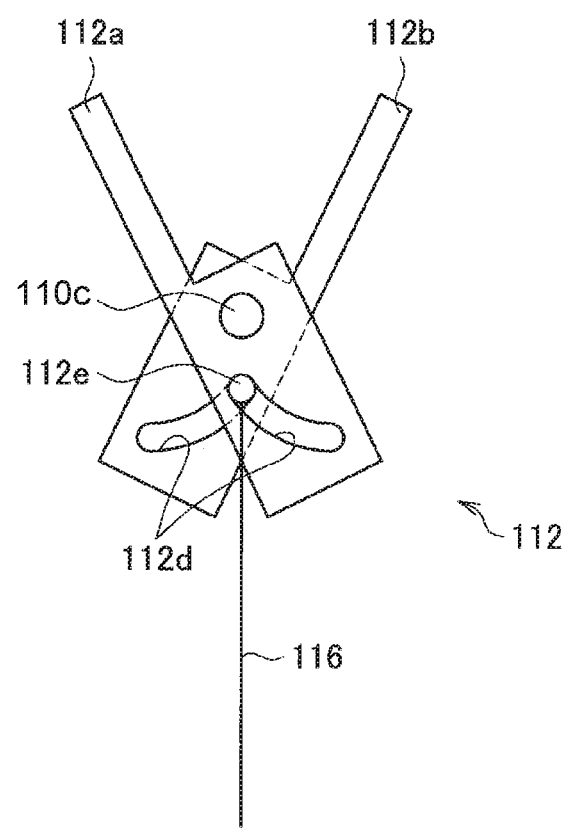
FIG. 2 is a schematic diagram illustrating a configuration of an end effector.

FIG. 2 is a schematic diagram illustrating a configuration of the end effector (contact portion) 112. The end effector 112 includes two blades 112a and 112b, and has a configuration in which a cam follower 112e moves along cam grooves 112d provided in the respective blades 112a and 112b, in accordance with pulling out of a cable 116 that is performed by the drive mechanism unit 120. With this configuration, the two blades 112a and 112b rotate around a shaft 110c in directions opposite to each other, which generates grip force. The body tissue 250 can be thereby gripped. Together with the detachable portion 114, the cable 116 functions as a transmission unit that transmits drive force generated by the drive mechanism unit 120, to the end effector 112.

The detachable portion 114 and the drive mechanism unit 120 are attached or detached by a coupling unit 200 that can adjust interlocking force by interlocking tolerance. The coupling unit 200 is configured so that grip force equal to or larger than a threshold value is not generated. More specifically, the coupling unit 200 has a configuration in which force is exerted on the coupling unit 200 in a pull-out direction by the tension of the cable 116 when grip force is added, and the coupling unit 200 is automatically detached when force exceeding interlocking force is generated. In other words, the coupling unit 200 is configured as a limiter mechanism that imposes restriction on the transmission of drive force generated by the drive mechanism unit 120, to the end effector 112. A limit value of grip force can be controlled by adjusting interlocking force in accordance with interlocking tolerance and a material sliding property. Relationship between interlocking tolerance and a material sliding property, and interlocking force can be obtained in advance through experiment or the like.

Figure 3:
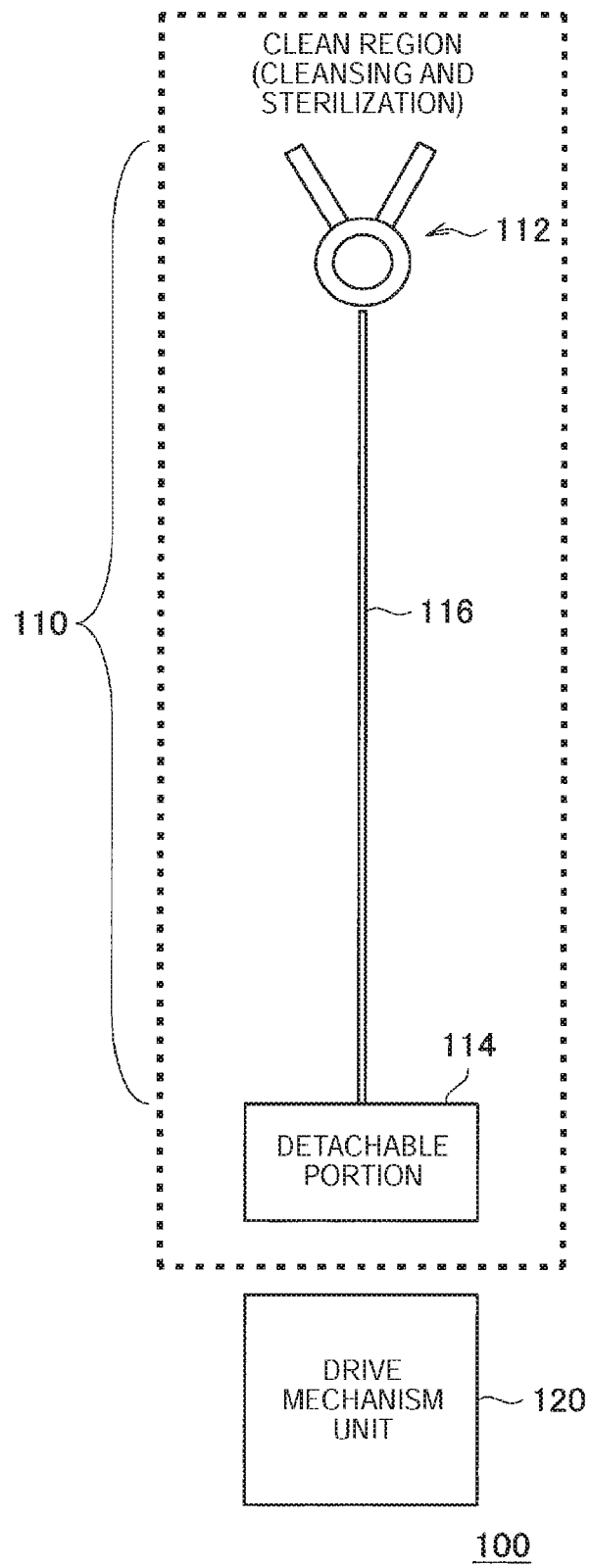
FIG. 3 is a schematic diagram illustrating a state in which a coupling unit is detached, and a surgical tool unit and a drive mechanism unit are separated.

FIG. 3 is a schematic diagram illustrating a state in which the coupling unit 200 is detached, and the surgical tool unit 110 and the drive mechanism unit 120 are separated. Here, the surgical tool unit 110 corresponds to a cleansing region, and in a state in which the surgical tool unit 110 and the drive mechanism unit 120 are separated, cleansing and sterilization of only the surgical tool unit 110 can be performed.

2. Configuration of Coupling Unit

Figure 4:
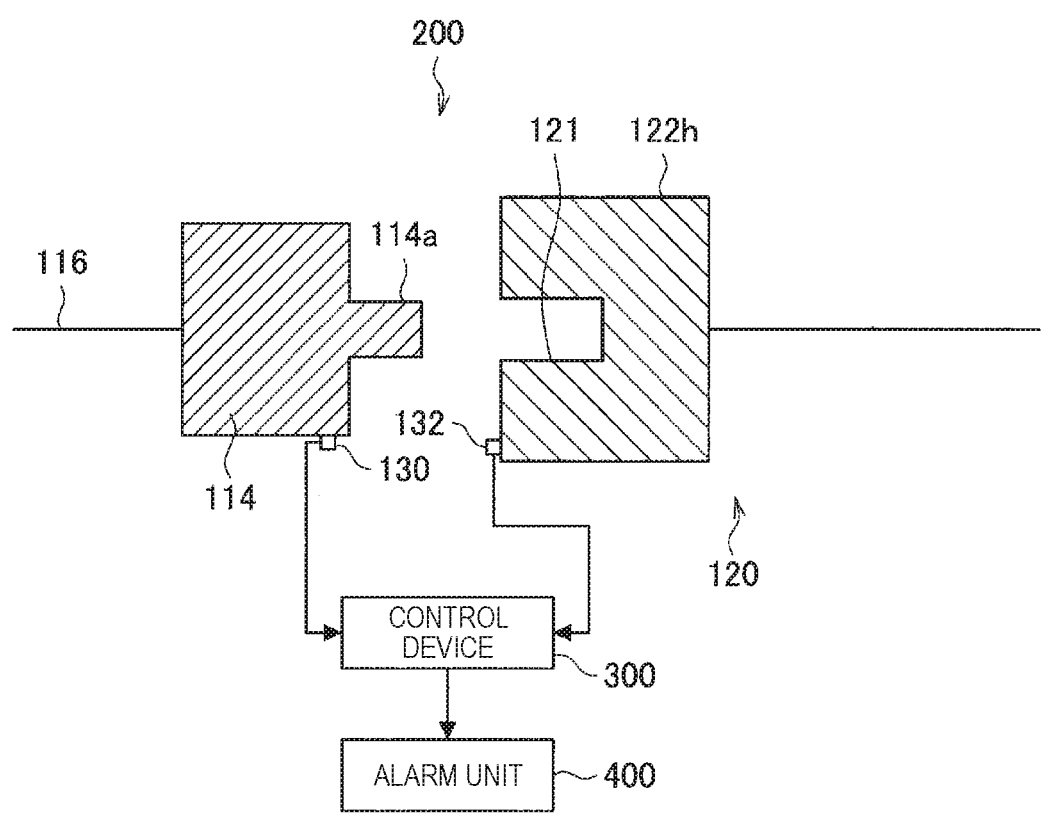
FIG. 4 is a schematic diagram illustrating a configuration of the coupling unit.

FIG. 4 is a schematic diagram illustrating a configuration of the coupling unit 200. The coupling unit 200 includes a boss (protruding portion) 114a provided on the detachable portion 114, and a boss hole (an insertion hole) 121 provided in a drive member 122h of the drive mechanism unit 120. The boss 114a is inserted into the boss hole 121, and interlocking force is generated between the boss 114a and the boss hole 121 by the interlocking tolerance and the material sliding property, so that the boss 114a is coupled to the boss hole 121.

If the boss 114a is inserted into the boss hole 121, a contactor 130 including conductive material that is provided on the detachable portion 114, and a contactor 132 including conductive material that is provided on the drive member 122h come into contact with each other, and the contactors 130 and 132 are electrically connected to each other. If the detachable portion 114 and the drive member 122h are separated, the contactor 130 and the contactor 132 become noncontact. If the detachable portion 114 and the drive member 122h are separated, a control device 300 issues an alarm from an alarm unit 350 on the basis of a conduction state of the contactor 130 and the contactor 132. The alarm can be issued through audio, display performed on a display or the like, etc. On the basis of the alarm, a user can recognize that grip force equal to or larger than the threshold value is generated in the end effector 112, and a detachable portion 110 is detached from the drive mechanism unit 120.

In addition, in the present embodiment, a configuration in which the boss 114a is provided on the detachable portion 114, and the boss hole 121 is provided in the drive member 122h is employed. Alternatively, a boss hole may be provided in the detachable portion 114, and a boss may be provided on the drive member 122h.

3. Configuration of Drive Mechanism Unit

Figure 5:
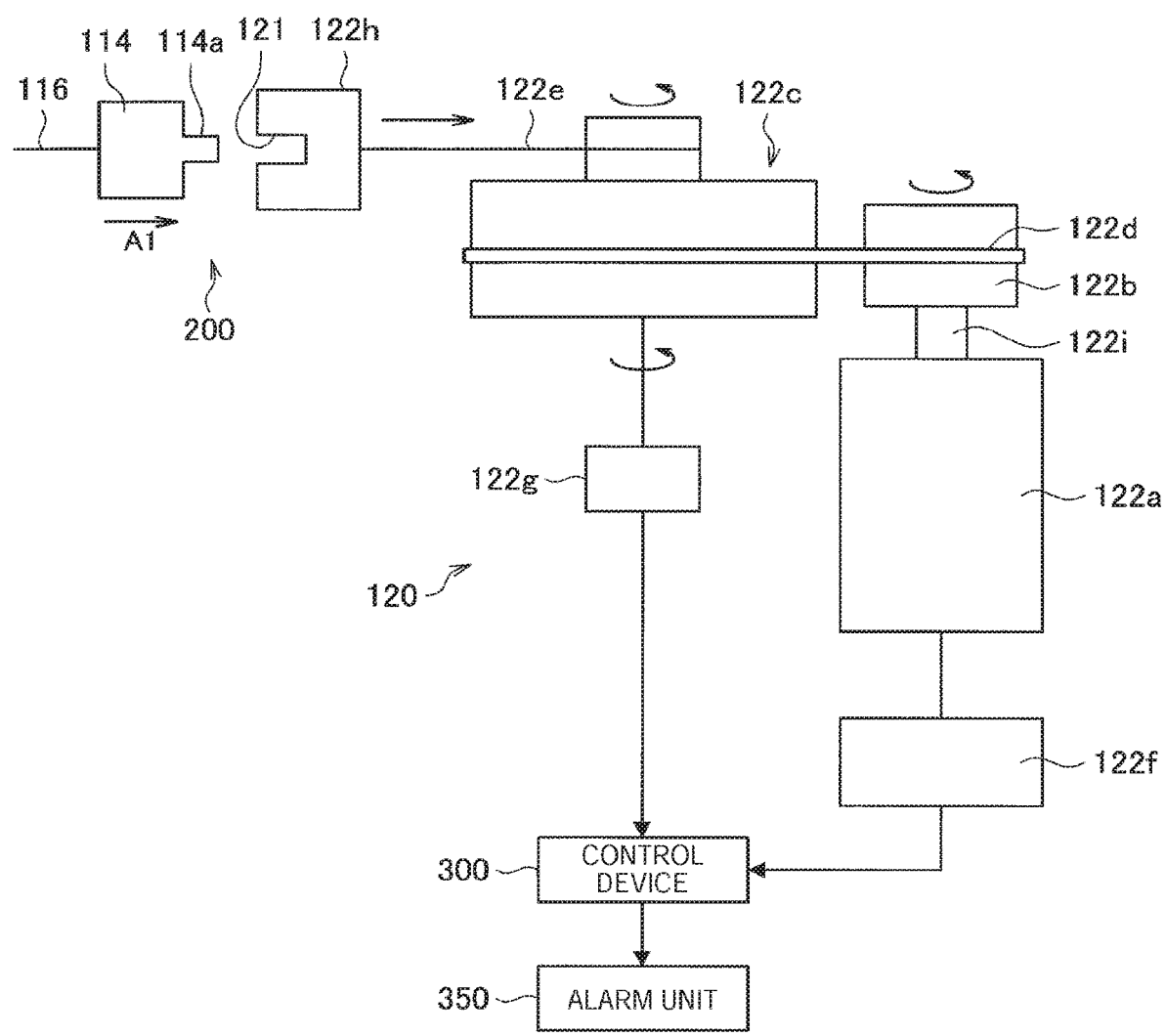
FIG. 5 is a schematic diagram illustrating a configuration of the drive mechanism unit.

FIG. 5 is a schematic diagram illustrating a configuration of the drive mechanism unit 120. As illustrated in FIG. 5, the drive mechanism unit 120 includes a motor 122a, a pulley 122b, a pulley 122c, a belt 122d, a belt 122e, a rotation number sensor 122f, a rotation number sensor 122g, and the drive member 122h provided with the boss hole 121.

In a configuration illustrated in FIG. 5, if the motor 122a drives the pulley 122b to rotate, the pulley 122c rotates via the belt 122d. Then, the rotation of the pulley 122c is transmitted to the drive member 122h via the belt 122e, and the boss 114a inserted in the boss hole 121 is driven in an arrow A1 direction. The cable 116 coupled to the detachable portion 114 is thereby driven in the arrow A1 direction as well, and the two blades 112a and 112b are driven.

At this time, if grip force applied by the two blades 112a and 112b becomes equal to or larger than the threshold value, interlocking between the boss 114a and the boss hole 121 is released, and the detachable portion 114 is detached from the drive member 122h of the drive mechanism unit 120. The surgical tool unit 110 and the drive mechanism unit 120 are thereby separated as illustrated in FIG. 3. Thus, because the detachable portion 114 is detached from the drive mechanism unit 120 if grip force equal to or larger than the threshold value is generated in the end effector 112, the body tissue 250 can surely avoid being gripped with grip force equal to or larger than the threshold value.

Here, for example, grip force required at the time of angiostomy in neurosurgical operation is about 0.5 N, and force required for clipping is about 2 N. Thus, setting interlocking force of the coupling unit 200 in accordance with these forces can prevent grip force equal to or larger than 0.5 N from being applied at the time of angiostomy, and can also prevent clipping from being performed with force equal to or larger than 2 N.

In this manner, because grip-target body tissue varies depending on surgery, an operator can prevent tissue damage caused by gripping, by selecting a torque limiter value that can generate desired grip force, in accordance with surgery. In addition, in a case where excess tension is applied to the cable 116, plastic elongation and break risk can occur in the cable 116. Nevertheless, a torque limiter mechanism formed by the coupling unit 200 can reduce these risks.

As an example, the boss 114a includes resin material, and the drive member 122h includes metal material. In addition, diameter tolerance of the boss hole 121 is assumed to be only one type, a plurality of detachable portions 114 having different tolerances for diameters of bosses 114a are prepared, and a detachable portion 114 having a boss 114a with optimum diameter tolerance is selected in accordance with a grip force limit value. Interlocking force and grip force corresponding to the interlocking force are obtained in advance for each of the plurality of detachable portions 114. From among the plurality of detachable portions 114, a detachable portion 114 having an optimum grip force limit value can be thereby selected in accordance with the type of surgery. In addition, interlocking force of the boss 114a, for example, can be adjusted by applying different coatings on the surface of the boss hole 121.

When cleansing and sterilization of the clean region are performed after surgery, detaching the coupling of the coupling unit 200 can separate the clean region and an unclean region, so that cleansing and sterilization of the surgical tool unit 110 being the clean region can be performed.

After the coupling of the coupling unit 200 is detached for ensuring safety at the time of overload, by reinserting the boss 114a into the boss hole 121 and coupling the boss 114a and the boss hole 121, return to surgery can be promptly achieved as soon as the safety is confirmed.

In addition, the torque limiter mechanism of the end effector 112 may be formed by slip of a shaft 122i of the motor 122a and the pulley 122b. In this case, interlocking between the boss 114a and the boss hole 121 is fixed so as not to be released. The pulley 122b is not fixed on the shaft 122i, and interlocking tolerance and a material sliding property of the pulley 122b and the shaft 122i are decided and interlocking force between the pulley 122b and the shaft 122i is adjusted so that the pulley 122b idles with respect to the shaft 122i if grip force equal to or larger than the threshold value is generated in the end effector 112.

With this configuration, if grip force equal to or larger than the threshold value is generated in the end effector 112, the pulley 122b idles with respect to the shaft 122i. Thus, the body tissue 250 can surely avoid being gripped with grip force equal to or larger than the threshold value. In other words, an interlocking portion of the shaft 122i and the pulley 122b is configured as a limiter mechanism that imposes restriction on the transmission of drive force generated by the motor 122a of the drive mechanism unit 120, to the end effector 112.

In the configuration illustrated in FIG. 5, a rotation number of the shaft 122i of the motor 122a that has been detected by the rotation number sensor 122f and a rotation number of the pulley 122c that has been detected by the rotation number sensor 122g are input to the control device 300. In a case where a ratio between the rotation number of the shaft 122i and the rotation number of the pulley 122c does not correspond to a speed reduction ratio between the pulley 122b and the pulley 122c, the control device 300 determines that the pulley 122b is idling with respect to the shaft 122i, and issues an alarm from the alarm unit 350. On the basis of the alarm, the user can recognize that grip force equal to or larger than the threshold value has been generated in the end effector 112.

In addition, in the aforementioned example, a configuration of driving the end effector 112 using the cable 116 has been described. Alternatively, a link structure may be used in place of the cable 116.

4. Example of Application to Mechanism of Driving Link Structure Using Cable

Figure 6:
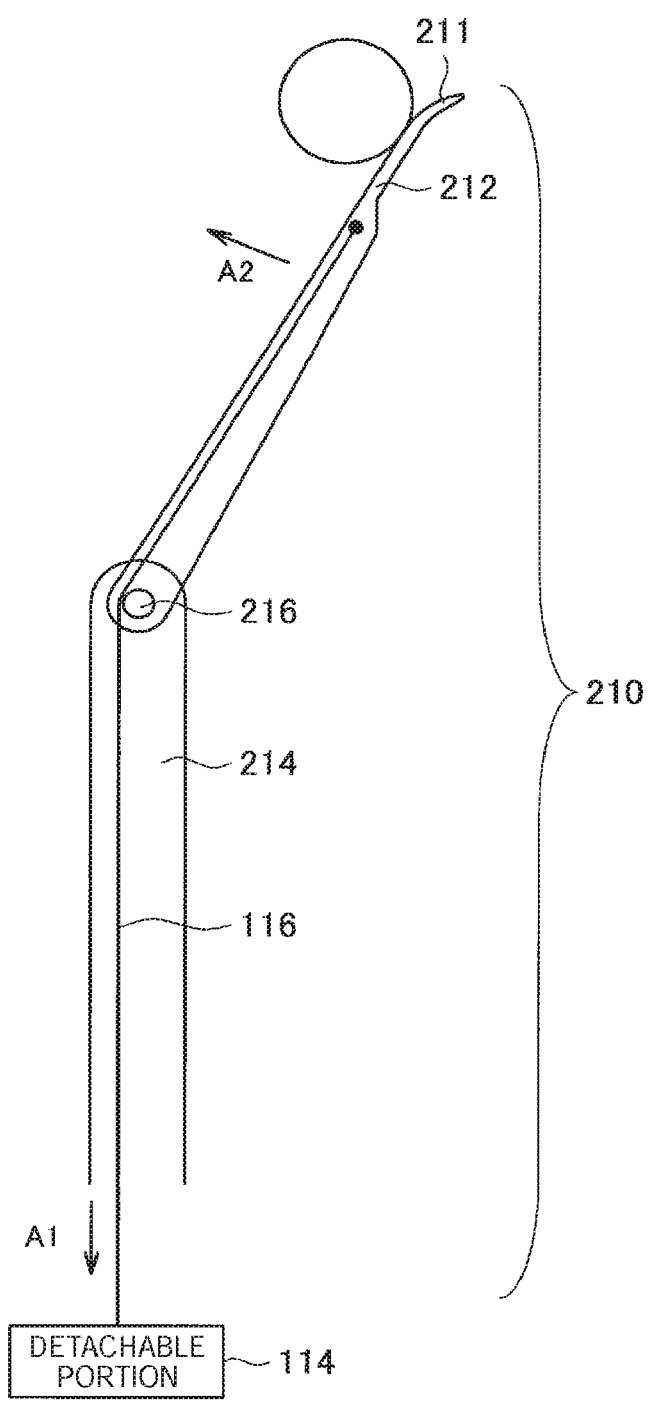
FIG. 6 is a schematic diagram illustrating an example of a mechanism of driving a link structure using a cable.

In addition, in the aforementioned example, a configuration of driving the end effector 112 using the cable 116 has been described. Alternatively, the present technology can also be applied to a mechanism of driving a link structure using the cable 116. FIG. 6 is a schematic diagram illustrating an example of a mechanism of driving a link structure using the cable 116. In the example illustrated in FIG. 6, a surgical tool unit 210 is different from the surgical tool unit 110 illustrated in FIG. 1, and the surgical tool unit 210 includes a link mechanism. In addition, in the example illustrated in FIG. 6, the surgical tool unit 210 includes a spatula (pressing member) 211 in place of an end effector. For example, the spatula 211 is used for pressing the body tissue 250 from a certain direction.

As illustrated in FIG. 6, an arm 212 is configured to be rotatable around a shaft 216 with respect to an arm 214. The spatula 211 is provided at the end of the arm 212. One end of a wire 116 is fixed to the detachable portion 114 similarly to FIG. 1. In addition, the other end of the wire 116 is connected to the arm 212.

In a configuration illustrated in FIG. 6, if the cable 116 is driven in an arrow A1 direction, the arm 212 rotates in an arrow A2 direction around the shaft 216. The body tissue 250 is thereby pressed by the spatula 211 provided at the end of the arm 212.

Also in the configuration illustrated in FIG. 6, by using the torque limiter mechanism formed by the coupling unit 200, the boss 114a and the boss hole 121 can be configured to be detached in a case where pressing force added on the body tissue 250 becomes equal to or larger than a predetermined value. With this configuration, force equal to or larger than the predetermined value can be prevented from being added to the body tissue 250.

In addition, also in the configuration illustrated in FIG. 6, the pulley 122b can be configured to idle with respect to the shaft 122i in a case where pressing force added on the body tissue 250 becomes equal to or larger than a predetermined value. With this configuration, force equal to or larger than the predetermined value can be prevented from being added to the body tissue 250.

5. Configuration Example of Surgical System

Figure 7:
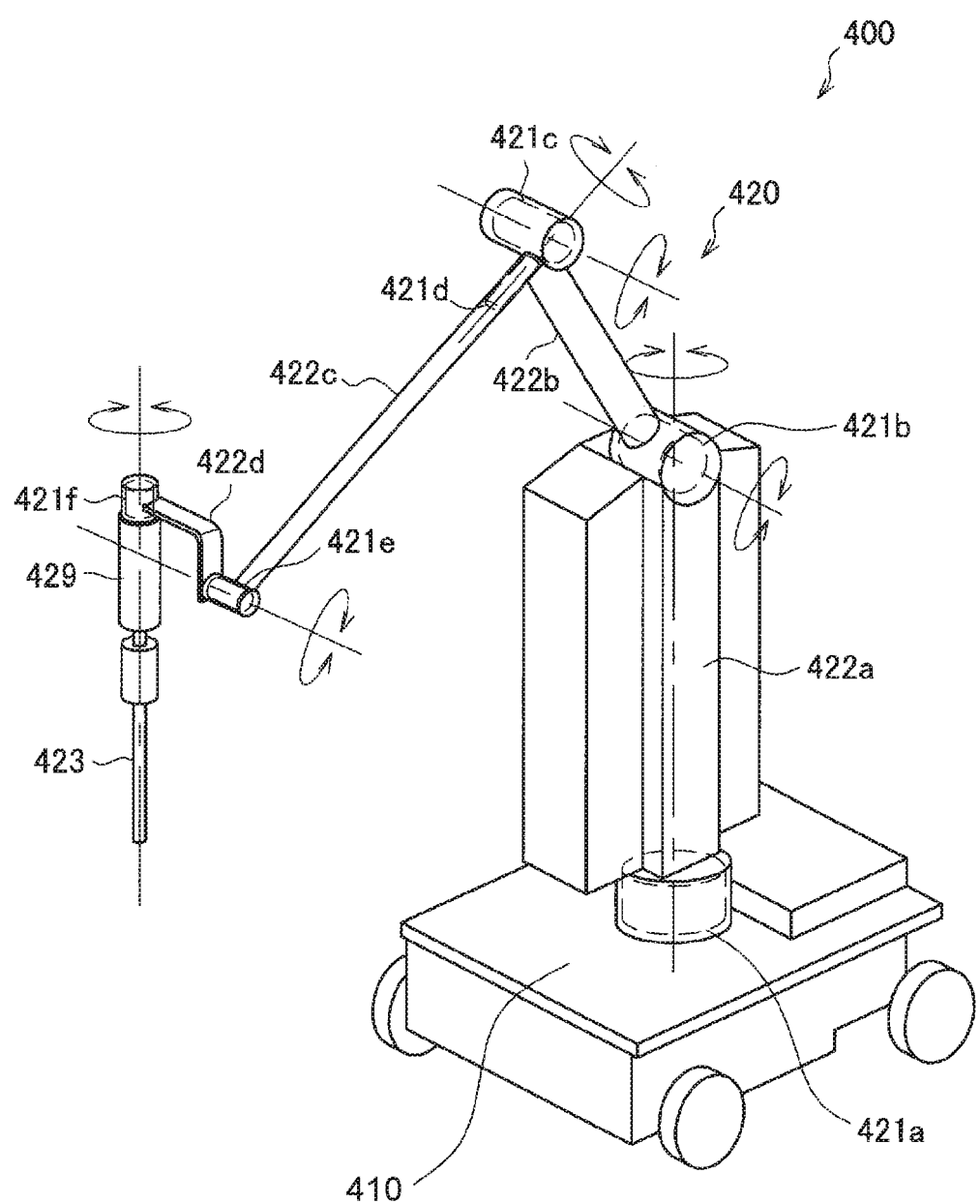
FIG. 7 is a schematic diagram illustrating a configuration example of a support arm device that can constitute a surgical system including the medical instrument illustrated in FIG. 1.

Next, a configuration example of a support arm device that can constitute a surgical system including the medical instrument 100 illustrated in FIG. 1 will be described with reference to FIG. 7. Referring to FIG. 7, a support arm device 400 includes a base portion 410, an arm unit 420, and the control device 300. The support arm device 400 is a medical support arm device that supports the medical instrument 100 such as a forceps during surgery.

The base portion 410 is a base of the support arm device 400, and the arm unit 420 extends from the base portion 410. The base portion 410 is provided with casters, and the support arm device 400 is grounded on a floor surface via the casters and is configured to be movable on the floor surface by the casters. Nevertheless, a configuration of the support arm device 400 according to the present embodiment is not limited to this example. For example, the support arm device 400 may have a configuration in which the base portion 410 is not provided, and the arm unit 420 is directly attached to a ceiling or a wall surface of a surgery room. For example, in a case where the arm unit 420 is attached to a ceiling, the support arm device 400 has a configuration in which the arm unit 420 is suspended from the ceiling.

The control device 300 that executes various types of information processing in the surgical system is provided inside the base portion 410. The control device 300 can be a processor such as, for example, a central processing unit (CPU) and a digital signal processor (DSP). Alternatively, the control device can be a control board or a microcomputer on which these processors and a storage element such as a memory are mounted. Various types of operations in the surgical system are executed by the processor constituting the control device, executing various types of signal processing in accordance with predetermined programs.

The control device 300 comprehensively controls the operations of the support arm device 400. The arm unit 420 includes a plurality of joint portions 421a, 421b, 421c, 421d, 421e, and 421f, a plurality of links 422a, 422b, 422c, and 422d that are rotatably coupled to each other by the joint portions 421a to 421e, and a retaining unit 429 rotatably provided at the end of the arm unit 420 via the joint portion 421f. In addition, the retaining unit 429 retains various types of medical instruments, and in the example illustrated in the drawing, a forceps 423 is attached to the retaining unit 429.

The links 422a to 422d are rod-shaped members, and one end of the link 422a is coupled to the base portion 410 via the joint portion 421a, the other end of the link 422a is coupled to one end of the link 422b via the joint portion 421b, and furthermore, the other end of the link 422b is coupled to one end of the link 422c via the joint portions 421c and 421d. Furthermore, the other end of the link 422c is coupled to one end of the substantially-L-shaped link 422d via the joint portion 421e, and the other end of the link 422d and the retaining unit 429 that retains the forceps 423 are coupled via the joint portion 421f. In this manner, the respective ends of the plurality of links 422a to 422d are coupled to each other by the joint portions 421a to 421f using the base portion 410 as a fulcrum. An arm shape extending from the base portion 410 is thereby formed.

The forceps 423 corresponds to the medical instrument 100 illustrated in FIG. 1 or 6 mentioned above. As mentioned above, the end of the forceps 423 is provided with the end effector 112 for gripping, cutting down, or performing other operations on the body tissue 250 of a patient. In performing surgery, positions and attitudes of the arm unit 420 and the forceps 423 are controlled by the support arm device 400 so that the forceps 423 can take desired position and attitude with respect to the body tissue 250 of the patient.

As described above, according to the present embodiment, by mechanistically setting a torque limiter (limiter mechanism), excess force application to the body tissue 250 can be suppressed, and safety can be enhanced. In addition, by forming the limiter mechanism using interlocking force generated in accordance with interlocking tolerance and a material sliding property, failure risk can be suppressed to the minimum. Thus, reliability can be drastically enhanced as compared with a method of detecting grip force using an electric sensor or the like. With this configuration, it becomes unnecessary for an operator to consider overload on the body tissue 250. The operator can therefore concentrate on surgery. In addition, force limit can be surely provided as compared with a method in which an operator estimates, on the basis of past surgery experience, force added to body tissue, from an amount of deformation of the body tissue that is caused when the body tissue is gripped, using an endoscopic image.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical instrument including:

a contact portion configured to contact body tissue;

a drive unit configured to generate drive force for causing the contact portion to contact the body tissue; and a limiter mechanism configured to impose restriction on transmission of the drive force to the contact portion, in accordance with contact force of the contact portion with respect to the body tissue.

(2)

The medical instrument according to (1), including:

a transmission unit configured to transmit the drive force generated by the drive unit, to the contact portion;

a protruding portion provided on one of the transmission unit and the drive unit; and an insertion hole provided in another one of the transmission unit and the drive unit, and into which the protruding portion is to be inserted, in which the drive force is transmitted to the contact portion by the drive unit pulling the transmission unit, and the limiter mechanism is formed by the protruding portion being detached from the insertion hole if contact force of the contact portion with respect to the body tissue becomes larger than a predetermined threshold.

(3)

The medical instrument according to (1), including:

a transmission unit configured to transmit the drive force generated by the drive unit, to the contact portion, in which the drive unit includes a motor, and a rotation member configured to be driven by the motor to drive the transmission unit, and the limiter mechanism is formed by the rotation member slipping with respect to rotation of the motor if contact force of the contact portion with respect to the body tissue becomes larger than a predetermined threshold.

(4)

The medical instrument according to (2), in which the contact portion includes an end effector configured to grip the body tissue.

(5)

The medical instrument according to (4), in which the threshold is set in accordance with a grip target of the end effector.

(6)

The medical instrument according to any one of (1) to (3), in which the contact portion includes a pressing member configured to press the body tissue.

(7)

The medical instrument according to any one of (2), (4), and (5), in which, if the protruding portion is detached from the insertion hole, a cleansable clean region at least including the contact portion and the transmission unit is separated.

(8)

The medical instrument according to any one of (1) to (9), including:
an alarm unit configured to issue an alarm if the limiter mechanism operates.

(9)

A surgical system including:
a medical instrument used for a patient; and
a support arm device configured to support the medical instrument,
in which the medical instrument includes
a contact portion configured to contact body tissue,
a drive unit configured to generate drive force for causing the contact portion to contact the body tissue, and
a limiter mechanism configured to impose restriction on transmission of the drive force to the contact portion, in accordance with contact force of the contact portion with respect to the body tissue.

REFERENCE SIGNS LIST 100, 200 medical instrument
110, 210 surgical tool unit
112 end effector
114 detachable portion
114a boss
116 cable
120 drive mechanism unit
121 boss hole
122a motor
122b pulley
122h drive member
122i shaft
200 coupling unit
211 spatula
250 body tissue
350 alarm unit
400 support arm device

The invention claimed is:

1. A medical instrument comprising:
a contact portion configured to contact body tissue;
a drive unit configured to generate drive force for causing the contact portion to contact the body tissue;
a limiter mechanism configured to impose restriction on transmission of the drive force to the contact portion, in accordance with contact force of the contact portion with respect to the body tissue; and
a transmission unit configured to transmit the drive force generated by the drive unit to the contact portion,
wherein the drive unit includes a motor having a shaft, and a rotation member, comprising a pulley, configured to be driven by the shaft of the motor to drive the transmission unit,
the limiter mechanism is formed by the pulley slipping with respect to rotation of the shaft of the motor if contact force of the contact portion with respect to the body tissue becomes larger than a predetermined threshold, and
the slipping of the rotation member is caused by interlocking tolerance and material sliding properties of the pulley and of the shaft.

2. The medical instrument according to claim 1, comprising:
a transmission unit configured to transmit the drive force generated by the drive unit, to the contact portion;
a protruding portion provided on one of the transmission unit and the drive unit; and
an insertion hole provided in another one of the transmission unit and the drive unit, and into which the protruding portion is to be inserted,
wherein the drive force is transmitted to the contact portion by the drive unit pulling the transmission unit, and
the limiter mechanism is formed by the protruding portion being detached from the insertion hole if contact force of the contact portion with respect to the body tissue becomes larger than a predetermined threshold.

3. The medical instrument according to claim 2, wherein the contact portion includes an end effector configured to grip the body tissue.

4. The medical instrument according to claim 3, wherein the threshold is set in accordance with a grip target of the end effector.

5. The medical instrument according to claim 2, wherein, if the protruding portion is detached from the insertion hole, a cleansable clean region at least including the contact portion and the transmission unit is separated.

6. The medical instrument according to claim 1, wherein the contact portion includes a pressing member configured to press the body tissue.

7. The medical instrument according to claim 1, comprising:
an alarm unit configured to issue an alarm if the limiter mechanism operates.

8. A surgical system comprising:
a medical instrument used for a patient; and
a support arm device configured to support the medical instrument,
wherein the medical instrument includes
a contact portion configured to contact body tissue,
a drive unit configured to generate drive force for causing the contact portion to contact the body tissue,
a limiter mechanism configured to impose restriction on transmission of the drive force to the contact portion, in accordance with contact force of the contact portion with respect to the body tissue, and
a transmission unit configured to transmit the drive force generated by the drive unit to the contact portion,
wherein the drive unit includes a motor having a shaft, and a rotation member, comprising a pulley, configured to be driven by the shaft of the motor to drive the transmission unit,
the limiter mechanism is formed by the pulley slipping with respect to rotation of the shaft of the motor if contact force of the contact portion with respect to the body tissue becomes larger than a predetermined threshold, and the slipping of the rotation member is caused by interlocking tolerance and material sliding properties of the pulley and of the shaft.

\* \* \* \* \*